(12) United States Patent
Niklason et al.

(10) Patent No.: US 8,198,245 B2
(45) Date of Patent: Jun. 12, 2012

(54) COMPOSITIONS AND METHODS FOR SOFT TISSUE AUGMENTATION

(75) Inventors: Laura Niklason, Greenwich, CT (US);
Yuling Li, Chapel Hill, NC (US);
Juliana Blum, Raleigh, NC (US);
Shannon Dahl, Durham, NC (US);
Geoffrey Erickson, Westport, CT (US);
Frank Zeigler, Encinitas, CA (US)

(73) Assignee: Humacyte, Inc., Research Triangle Park, NC (US)

( * ) Notice: Subject to any disclaimer, the term of this patent is extended or adjusted under 35 U.S.C. 154(b) by 26 days.

(21) Appl. No.: 12/220,420

(22) Filed: Jul. 24, 2008

(65) Prior Publication Data

US 2009/0028817 A1    Jan. 29, 2009

Related U.S. Application Data

(60) Provisional application No. 60/962,289, filed on Jul. 27, 2007.

(51) Int. Cl.
| | |
|---|---|
| *A61K 38/39* | (2006.01) |
| *A61K 31/726* | (2006.01) |
| *A61K 38/18* | (2006.01) |
| *C07K 14/78* | (2006.01) |

(52) U.S. Cl. ....... 514/18.8; 514/7.6; 424/93.7; 530/353; 530/356

(58) Field of Classification Search ................... None
See application file for complete search history.

(56) References Cited

U.S. PATENT DOCUMENTS

| | | | | |
|---|---|---|---|---|
| 3,895,106 | A | * | 7/1975 | Morrison ............. 514/54 |
| 4,424,208 | A | * | 1/1984 | Wallace et al. ........... 514/21 |
| 4,442,093 | A | * | 4/1984 | Maeda et al. ............ 514/167 |
| 4,832,693 | A | * | 5/1989 | Gloyer ................ 604/110 |
| 4,926,869 | A | * | 5/1990 | Rubin et al. ............ 424/1.49 |
| 5,223,420 | A | | 6/1993 | Rabaud et al. ........... 424/425 |
| 5,366,498 | A | * | 11/1994 | Brannan et al. .......... 623/23.73 |
| 5,705,488 | A | | 1/1998 | Janzen et al. ........... 514/21 |
| 6,537,567 | B1 | | 3/2003 | Niklason et al. ......... 424/423 |
| 6,962,814 | B2 | | 11/2005 | Mitchell et al. .......... 435/402 |
| 7,125,837 | B1 | * | 10/2006 | Keating et al. .......... 514/13.5 |
| 2004/0078090 | A1 | | 4/2004 | Binette et al. |
| 2005/0058629 | A1 | | 3/2005 | Harmon et al. |
| 2006/0093644 | A1 | | 5/2006 | Quelle et al. |
| 2007/0031474 | A1 | * | 2/2007 | Tayot ................. 424/433 |
| 2007/0071729 | A1 | | 3/2007 | Bernstein |
| 2008/0038306 | A1 | | 2/2008 | David |
| 2009/0028817 | A1 | | 1/2009 | Niklason et al. |

FOREIGN PATENT DOCUMENTS

| | | |
|---|---|---|
| JP | 2008074846 A | 4/2008 |
| RU | 2120307 C1 | 10/1998 |
| WO | WO 03/046055 | 6/2003 |
| WO | WO 2006/066327 | 6/2006 |

OTHER PUBLICATIONS

Collagen Product Information. Worthington Biochemical Corporation. Lakewood, NJ. [online] [retrieved on Apr. 9, 2010]. Retrieved from the Internet:<URL:http://www.worthington-biochem.com/CL/cat.html>.*
Daamen et al. Preparation and evaluation of molecularly-defined collagen-elastin-glycosaminoglycan scaffolds for tissue engineering. Biomaterials. Oct. 2003;24(22):4001-9.*
Sclafani et al. Evaluation of acellular dermal graft in sheet (AlloDerm) and injectable (micronized AlloDerm) forms for soft tissue augmentation. Clinical observations and histological analysis. Arch Facial Plast Surg. Apr.-Jun. 2000;2(2):130-6.*
Daamen et al. (2001), Biomaterials, 22:1997-2005.
Daamen et al. (2005), Tissue Engineering, 11:1168-1176.
Daamen et al. (2005), Biomaterials, 26:81-92.
Dahl (2003), Cell Transplantation, 12:659-666.
Database WPI Week 200012 (1998), Thomson Scientific, XP002514066.
Database WPI Week 200883 (2008), Thomson Scientific, XP002514351.
Hollinger et al. (1988), Calcified Tissue International, 42:231-236.
Lee et al. (2006), American Journal of Pathology, 168:490-498.
Lemperle et al. (2003), Aesthetic Plastic Surgery, 27:354-366.
Niklason et al. (1999), Science, 284:489-493.
Starcher et al. (1976), Analytical Biochemistry, 74:441-447.
Urry et al. (1976), Calcified Tissue Research, 21:57-65.
International Search Report for PCT/US2008/008970, mailed Feb. 17, 2009.

* cited by examiner

*Primary Examiner* — David Romeo
(74) *Attorney, Agent, or Firm* — Mintz Levin Cohn Ferris Glovsky and Popeo, P.C.; Ivor R. Elrifi

(57) ABSTRACT

The present invention provides compositions comprising isolated human collagen, isolated human elastin and a pharmaceutically acceptable carrier wherein the human elastin is substantially insoluble in water with a molecular weight greater than 100 kDa. The present invention further provides methods and kits for soft tissue augmentation.

20 Claims, 7 Drawing Sheets

Fig. 1: Gel of collagen from vascular tissue.

COMPOSITIONS AND METHODS FOR SOFT TISSUE AUGMENTATION

RELATED APPLICATIONS

This application claims the benefit of U.S. Provisional Application No. 60/962,289, filed on Jul. 27, 2007, the contents of which are incorporated herein by reference in its entirety.

FIELD OF THE INVENTION

This invention relates generally to compositions comprising isolated human collagen and isolated human elastin, and generally related to methods and kits for soft tissue augmentation using these compositions.

BACKGROUND OF THE INVENTION

Natural skin is composed of many elements, including dermal fibroblasts and keratinocytes, hair follicles, nerves and blood vessels. Extracellular matrix components of skin, which are responsible for the strength, elasticity and turgor of native, healthy skin, include collagens, elastin and glycosaminoglycans. Collagen molecules provide the bulk of the tensile properties of all connective tissues in the human body, including skin. Elastin is a very long-lived protein that nonetheless breaks down in the skin of older individuals. Elastin breakdown contributes to skin drooping and wrinkles. Hydration is retained in skin by the presence of glycosaminoglycans, which act as "sponges" to retain water and provide skin with its natural turgor. Without these critical extracellular matrix components, skin becomes thin, wrinkled, and weak.

Various forms of injectable products have been developed for skin and other soft tissue augmentation. These products fall into synthetic and "natural" categories, wherein natural materials are derived from animal or human tissues. Synthetic materials that have been used as tissue bulking agents include silicone, oils and waxes, but these materials suffer from healing complications and are very viscous and difficult to inject. Animal-derived materials that have been described include bovine collagen in injectable forms. However, bovine collagen induces occasional immune reactions in recipients, due to the fact that bovine collagens are not identical to human collagens and can serve as antigens for immune reactivity. Other animal-derived extracellular matrix materials include hyaluronic acid that is derived from rooster combs. This material is quite viscous and also has the drawback of being of non-human origin. Additionally, various preparations of elastin currently in use have the drawback of inducing calcification upon implantation.

The compositions and methods of the present invention address these problems and fulfill a long felt need in the art.

SUMMARY OF THE INVENTION

The present invention provides compositions comprising isolated human collagen, isolated human elastin and a pharmaceutically acceptable carrier where the human elastin is substantially insoluble in water with a molecular weight greater than 100 kDa. The composition can comprise isolated human collagen derived from engineered vascular tissue or derived from micro-bead culture. The composition can comprise isolated human elastin derived from engineered vascular tissue or native vascular tissue. The isolated human elastin can be cross-linked.

The compositions can include about 10-100 mg/ml of isolated human collagen, more preferably about 30 mg/ml of isolated human collagen. The isolated human collagen can have a molecular weight of about 100 to about 500 kDa. The compositions can include about 2 to about 60 mg/ml of isolated human elastin, preferably about 3 to 30 mg/ml of isolated human elastin.

The compositions can further include isolated human glycosaminoglycans. The compositions can further include one or more active agents selected from the group consisting of one or more anti-inflammatory agents, tissue formation agents, adipose tissue formation agents, anesthetics, antioxidants, heparin, epidermal growth factor, transforming growth factor, transforming growth factor-β, platelet-derived growth factor, fibroblast growth factor, connective tissue activating peptides, β-thromboglobulin, insulin-like growth factors, tumor necrosis factors, interleukins, colony stimulating factors, erythropoietin, nerve growth factors, interferons or combinations thereof. The compositions can further comprise one or more cells or tissues, preferably adipose tissue or dermal fibroblasts.

The present invention also provides dermal or subdermal fillers including isolated human collagen, isolated human elastin and a pharmaceutically acceptable carrier where the human elastin is substantially insoluble in water with a molecular weight greater than 100 kDa.

The compositions can further include elastin isolated from human non-frozen vascular tissue which is substantially insoluble in water. The compositions of the present invention do not induce calcification in vivo.

The present invention also provides methods for soft tissue augmentation in a subject comprising, administering a composition comprising isolated human collagen, isolated human elastin and a pharmaceutically acceptable carrier wherein the human elastin is substantially insoluble in water with a molecular weight greater than 100 kDa. The method of the soft tissue augmentation can improve conditions including, but not limited to, lines, folds, wrinkles, minor facial depressions, cleft lips, correction of minor deformities due to aging or disease, deformities of the vocal cords or glottis, deformities of the lip, crow's feet and the orbital groove around the eye, breast deformities, chin deformities, augmentation; cheek and/or nose deformities, acne, surgical scars, scars due to radiation damage or trauma scars, and rhytids. The soft tissue can be located in the pelvic floor, in the peri-urethral area, near the neck of the urinary bladder, or at the junction of the urinary bladder and the ureter. The method of soft tissue augmentation can increase tissue volume. The compositions may be injected into the skin or may be injected underneath the skin. The compositions include insoluble elastin derived from human vascular tissue that does not induce inflammatory or immune response and does not induce calcification.

The present invention also include kits and methods of using the kits for augmentation of a soft tissue. The present kits include isolated human collagen, isolated human elastin and a pharmaceutically acceptable carrier wherein the human elastin is substantially insoluble in water with a molecular weight greater than 100 kDa a syringe; a sterile wrapper surrounding said syringe and providing a sterile environment for said syringe and any other material and/or reagents necessary. The kits can also include agents selected from the group consisting of heparin, epidermal growth factor, transforming growth factor, transforming growth factor-β, platelet-derived growth factor, fibroblast growth factor, connective tissue activating peptides, β-thromboglobulin, insulin-like growth factors, tumor necrosis factors, interleukins, colony stimulating factors, erythropoietin, nerve growth factors, interferons, osteogenic factors and bone morphogenic proteins.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
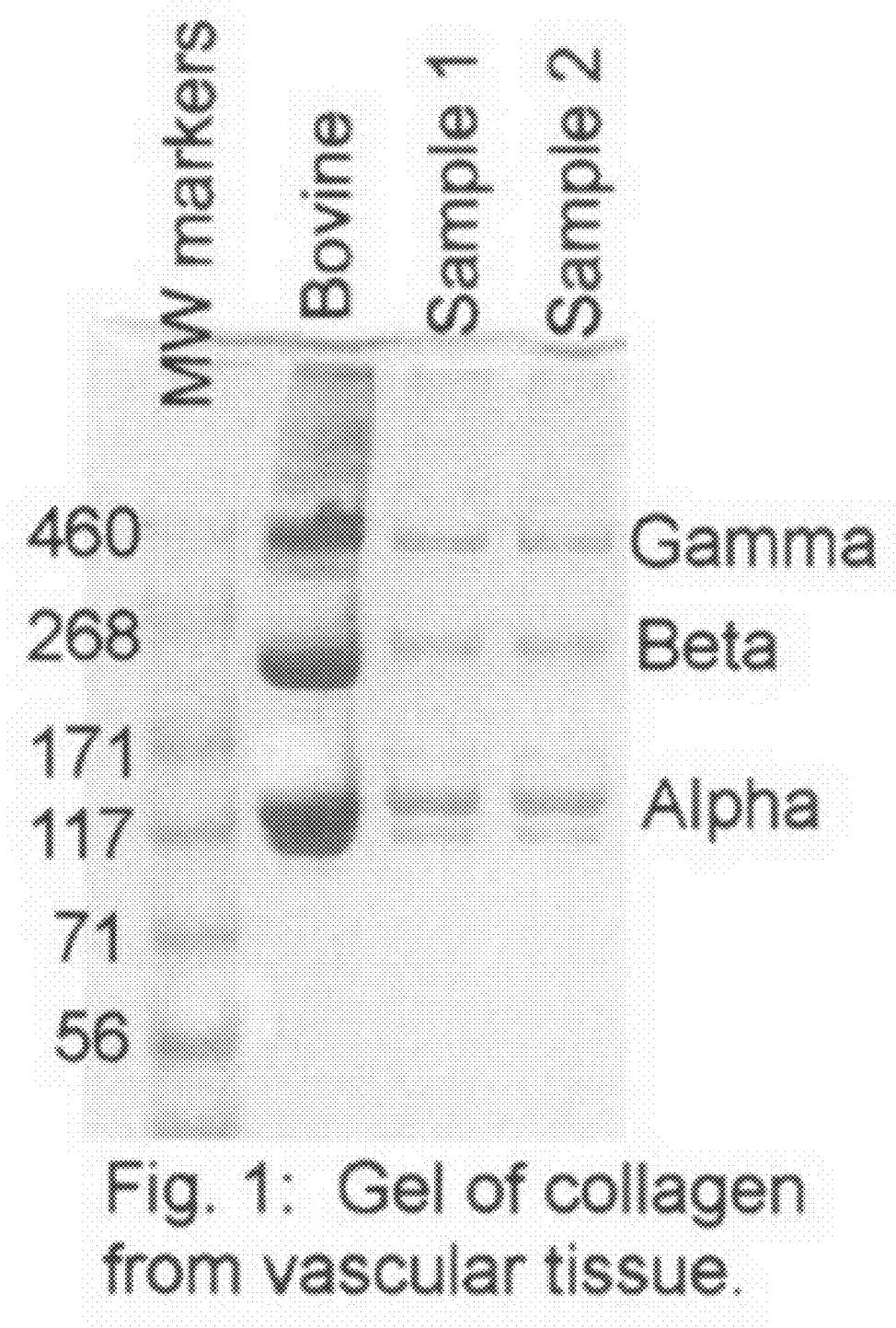
FIG. 1 illustrates the results of a polyacrylamide gel showing the very high levels of collagen purity in this preparation, as compared to the purified bovine collagen control.

The present invention provides compositions for the augmentation of skin and other soft tissues. Preferably, the compositions are formulated for injection. The compositions are composed of extracellular matrix components that are derived from vascular tissues, including, but not limited to, collagens, elastin and glycosaminoglycans. The extracellular matrix elements are combined in such a way as to improve their similarity to human skin extracellular matrix components, and also to increase their longevity in vivo and to minimize complications of administration. Deriving extracellular matrix from vascular tissues produces a "vascular-supporting" injectable formulation, which encourages host blood vessels to infiltrate and support the injected product. Such vascular-derived extracellular matrix compositions have the advantage of incorporating more easily into the host, and of stimulating the formation of nourishing blood vessels to the treated skin or other soft tissue. The extracellular matrix components are entirely of human origin, and may be derived from engineered or from native tissues. Unlike other injectable formulations for skin augmentation that contain only collagens or only animal-derived hyaluronans, these formulations contain other human extracellular matrix components that render them more similar to native, healthy human skin.

Soft Tissue Augmentation

Augmentation of soft tissue, such as skin, can be an important factor in recovering from injury or for cosmetic purposes. For example, with normal aging, skin may become loose or creases can form, such as nasal-labial folds. In the face, creases or lines may adversely affect a person's self esteem or even a career. Thus, there has been a need for compositions and methods that can diminish the appearance of creases or lines.

Further, there are situations in which loss of tissue can leave an indentation in the skin. For example surgical removal of a dermal cyst, lipoatrophy or solid tumor can result in loss of tissue volume. In other cases, injuries, such as gunshot wounds, knife wounds, or other excavating injures may leave an indentation in the skin. Regardless of the cause, it can be desirable to provide adermal filler that can increase the volume of tissue to provide a smoother or more even appearance.

One example for needed support is dermal augmentation in the face where dermal and subdermal volume is lost due to aging.

The term "soft tissue augmentation" includes, but is not limited to, the following: dermal tissue augmentation; filling of lines, folds, wrinkles, minor facial depressions, cleft lips and the like, especially in the face and neck; correction of minor deformities due to aging or disease, including in the hands and feet, fingers and toes; augmentation of the vocal cords or glottis to rehabilitate speech; hemostatic agent, dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; bulking agent for periurethral support, filling of indentations in the soft tissue, dermal or subcutaneous, due to, e.g., overzealous liposuction or other trauma; filling of acne or traumatic scars and rhytids; filling of nasolabial lines, nasoglabellar lines and infraoral lines. Moreover, the present invention can be directed to hard tissue augmentation. The term "hard tissue" includes but is not limited to bone, cartilage and ligament.

The soft tissue can be located in the pelvic floor, in the peri-urethral area, near the neck of the urinary bladder, or at the junction of the urinary bladder and the ureter.

The term "augmentation" means the repair, decrease, reduction or alleviation of at least one symptom or defect attributed due to loss or absence of tissue, by providing, supplying, augmenting, or replacing such tissue with the compositions of the present invention. The compositions of the present invention can also be used to prevent at least one symptom or defect.

Dermal fillers are used to fill scars, depressions and wrinkles. Dermal filler substances have various responses in the dermis from phagocytosis to foreign body reactions depending on the material (Lemperle et al., Aesthetic Plast. Surg. 27(5):354-366; discussion 367 (2003)). One goal of dermal fillers is to temporarily augment the dermis to correct the surface contour of the skin without producing an unacceptable inflammatory reaction, hypersensitivity reaction or foreign body reaction that causes pain, redness or excessive scar formation for a period of time.

The ideal material for human skin augmentation would include one or more of the critical extracellular matrix elements that provide skin its mechanical properties. These elements include collagen, elastin and glycosaminoglycans. In addition, to obviate immune responses, these materials should optimally be of human origin. Human materials will also induce less inflammatory reaction than animal-derived materials, and hence will be likely to persist longer after injection into the recipient, thereby extending and improving the cosmetic effect of a formulation suitable for injection.

Many types of dermal filling procedures can benefit from the use of the compositions of the present invention. The uses of the present invention are designed (but not limited) to be used to provide increased volume of a tissue that, through disease, injury or congenital property, is less than desired. Compositions can be made to suit a particular purpose, and have desired retention times and physical and/or chemical properties.

Exemplary uses of compositions of this invention can be particularly desirable to fill facial tissue (e.g., nasolabial folds), to increase the volume of the dermis in the lips, nose, around the eyes, the ears and other readily visible tissue. Additionally, the compositions can be desirably used to provide bulk to increase the volume of skin secondary to excavating injuries or surgeries. For example, the site around a dermal cyst can be filled to decrease the appearance of a dimple at the site of surgery.

As such, the present invention provides methods of skin augmentation by administering the extracellular matrix compositions of the invention to a subject in need thereof. Preferably, the methods improve skin wrinkles and/or increase skin volume. The subject or patient treated by the methods of the invention is a mammal, more preferably a human. The following properties or applications of these methods will essentially be described for humans although they may also be applied to non-human mammals, e.g., apes, monkeys, dogs, mice, etc. The invention therefore can also be used in a veterinarian context.

Extracellular Matrix Protein Compositions

The present invention provides compositions comprising isolated human collagen, isolated insoluble human elastin and a pharmaceutically acceptable carrier. These compositions may include additional proteins and active agents as described in further detail herein.

The compositions of the present invention which combine collagen with other elements of native skin, such as elastin, and in some embodiments, glycosaminoglycans, provide superior tissue augmentation, elasticity and turgor, as compared to compositions comprising a single extracellular matrix component (e.g. collagen). These compositions comprising isolated human collagen and elastin provide increased persistence in vivo as compared to compositions comprising collagen alone, due to the improved similarity of the collagen/elastin matrix to natural human skin.

Further, as the extracellular matrix components are derived from human vascular tissues that are subjected to decellularization prior to isolation of extracellular matrix components, the compositions provide longer persistence and retention in vivo (due to less inflammatory breakdown), and will be less prone to inflammation, calcification, and immune reaction, than components derived from animal sources and isolated without a decellularization step.

With respect to calcification, this complication is known to exist for various purified forms of elastin, though the mechanism that causes the calcification remains unclear (Lee, et al., American Journal of Pathology 2006; 168: 490-498; Daamen et al., Biomaterials 2005; 26: 81-92; Hollinger et al., Calcified Tissue International 1988; 42: 231-236; Urry et al., Calcified Tissue Research 1976; 21: 57-65). Competing hypotheses for elastin calcification advanced by those skilled in the art include the intrinsic nature of elastin pentapeptides to induce calcification, the central role of metalloproteinases in inducing calcification and the central role of microfibril impurities in elastin calcification. However, the precise cause of elastin calcification in vivo remains unknown.

Collagen

The compositions of the present invention include an effective amount of isolated human collagen and a pharmaceutically acceptable carrier. Preferably, the human collagen is derived from engineered tissue in vitro and has a molecular weight of approximately 100 kDa to approximately 500 kDa. Preferably, the compositions of the present invention comprise about 10 mg/mL-100 mg/mL of isolated human collagen, preferably about 15 mg/ml-70 mg/ml of isolated human collagen, more preferably about 20 mg/ml-60 mg/ml of isolated human collagen and most preferably 30 mg/ml of isolated human collagen.

To produce isolated human collagen, human vascular cells are cultured in vitro so as to maximize their production of collagenous matrix. This is accomplished by a combination of carefully selected growth factors and culture medium components, combined with physical stimuli of cells (such as stretching, shearing or stirring) to increase collagen matrix synthesis (see, for example U.S. Pat. No. 6,537,567). This cultured tissue is then subjected to a decellularization process that removes cellular components and leaves behind a mostly collagen-based extracellular matrix (see, for example U.S. Pat. No. 6,962,814). The collagen in this matrix can then isolated by one of several methods known in the art.

The collagen derived as described above has several advantages over collagen derived from native tissues or using previously-described methods to derive engineered collagen. Engineered tissues are derived from cells that are banked and highly screened for infectious agents, which makes this material generally safer than materials derived from cadavers. Also, the material is derived from vascular smooth muscle cells, resulting in a "vascular-friendly" extracellular matrix material that supports the formation of nourishing blood vessels. Further, this method for collagen isolation incorporates a decellularization step, whereby cellular components and proteins are actively removed from the collagen matrix. This provides a highly pure collagen matrix product (at least 70-80% purity as determined by any assay known in the art, such as SDS PAGE analysis) and decreases the potential for immune reaction to non-extracellular matrix components.

Elastin

The compositions of the present invention also include an effective amount of isolated human elastin and a pharmaceutically acceptable carrier. Preferably, the compositions of the present invention comprise human elastin that is cross-linked and insoluble. Further, it is preferable that the compositions of the present invention comprise human elastin that has a molecular weight of approximately 100 kDa, and more preferably greater then 100 kDa, as determined by any assay known in the art such as SDS PAGE analysis. Moreover, the compositions of the present invention comprise a particle size less than about 200 μm, preferably less than about 100 μm, more preferably less than about 50 μm. The compositions comprise about 2-60 mg/ml of isolated human elastin, preferably 3-30 mg/ml of isolated human elastin. The isolated cross-linked elastin is substantially insoluble in water, wherein the water-soluble elastin content is in the range of 0.1-10 wt %, preferably in the range of 0.1-8 wt %, more preferably in range of 0.1-6 wt %, more preferably in the range of 0.1-4 wt %, more preferably in the range of 0.1-2 wt % and most preferably in the range of 0.1-1 wt %. Alternatively, the elastin is completely insoluble in water. In some embodiments, it is preferable to have elastin with amino acid length which permits the persistence of the protein in vivo.

To produce isolated human elastin, human vascular cells are cultured in vitro so as to maximize their production of cross-linked elastin. The cross-linked elastin will be insoluble and will permit the persistence of the protein in vivo. While there are multiple reports of cells producing non-crosslinked tropoelastin monomers in culture, it is known to be very difficult to stimulate the formation of cross-linked elastin from human vascular cells in vitro. However, the present invention provides culture conditions whereby creation of insoluble elastin is achieved, as documented by the presence of desmosine cross-links that are specific to elastin. These tissues that contain elastin may then be subjected to a decellularization process (as described above for collagen), after which the elastin is collected from the remaining matrix using any one of several standard techniques known in the art.

The purity of elastin is typically assessed by the profile of amino acids in the final product, and by the presence of desmosine cross-links, which are specific for cross-linked and insoluble elastin. The amino acid compositions of elastin from various species have been reported (Starcher et al., Analytical Biochemistry 1976; 74: 441-447). In particular, it is known that alanine residue concentrations of greater than 200/1000 total residues, and valine residues of greater than 70/1000 total residues, are consistent with highly pure elastin (Daamen et al., Biomaterials 2001; 22: 1997-2005). However, many methods are reported for the isolation of purified elastin, and no consensus has been reached regarding the optimal method for elastin isolation and implantation (Daamen, W. F., Hafmans, T., Veerkamp, J. H., van Kuppevelt, T. H., "Isolation of intact elastin fibers devoid of microfibrils", Tissue Engineering 2005; 11: 1168-1176).

The elastin derived as described above has several advantages over previous reports of elastin isolation. The elastin would be derived from human, and not animal, origin. Since the cells used to produce the elastin are banked and derived from human vascular tissue, this will result in lower immunogenicity in the human recipients. The elastin thus generated is of a "vascular" type, which should also promote the infiltration of blood vessels into the treated area to support tissue reconstitution. The decellularization process, as with the collagen production, removes unwanted and potentially immunogenic cellular components from the elastin matrix. This provides a highly pure elastin matrix product (>70-80% purity and means that this elastin product has a lower propensity for immune reaction, inflammation, and calcification, which are known complications of implantation of xenogeneic elastins. Preferably, the isolated human elastin of the present invention comprises desmosine cross-links. More preferably, the desmosine cross-links are present in insoluble elastin at a ratio of above 10,000 picomoles per milligram of vascular tissue.

In addition to the methods described above, human elastin may also be isolated from native human blood vessels by means that ensure very high purity, and thus minimize chances for immune reaction, inflammation, and calcification. Indeed, calcification is one particular complication associated with elastin implantation, and hence having species matching and highly pure formations, that will minimize inflammatory response, are important to cosmetic outcome and function.

An immune and inflammatory response can be measured by various assays known in the art such as, but not limited to, MHC-peptide tetramer, ELISPOT, intracellular cytokine assay. In general, a 10-50% increase in T-lymphocytes over the base line level (e.g., wild type normal state), preferably a 50% increase in T-lymphocytes, more preferably a 40% increase in T-lymphocytes, and most preferably a 30% increase in T-lymophocyte production indicates a significant immune response.

Calcification levels can be measured by various assays known in the art such as, but not limited to, atomic spectroscopy and H&E and alizarin red staining. In general, 75-99% reduction in calcification, preferably 80% reduction in calcification, more preferably a 90% reduction in calcification, most preferably 95% reduction in calcification, indicates significant reduction in calcification with the compositions of the present invention as compared to other control forms of elastin such as purified bovine elastin (for example, from Elastin Products Co). That is, the compositions of the present invention do not induce significant calcification, e.g., calcification greater than 25%, preferably calcification between 5-20%, more preferably between 10 and 15% as compared to the vehicle control (or the wild type normal state in a subject prior to administration). Alternatively, calcification levels of elastin preparation are indistinguishable form vehicle control.

In this embodiment, human blood vessels are treated with a decellularization process that removes cellular components and glycosaminoglycans. Preferably, the human blood vessels are extracted from discarded human umbilical cords, but may be obtained from other parts of the body, including the aorta or other major arteries or veins.

The blood vessels thus treated consist primarily of collagen and elastin. Collagen may be removed from such treated blood vessels by any one of a number of methods known in the art, including autoclave treatment, pepsin digestion, collagenase digestion, high salt treatments, alkali treatments, etc. In this way, collagen matrix is removed and elastin is retained.

Glycosaminoglycans

The compositions of the present invention may also include an effective amount of one or more isolated human glycosaminoglycans and a pharmaceutically acceptable carrier. Human glycosaminoglycans may be isolated from engineered tissues. Engineered tissues, grown in serum-containing medium, produce an extracellular matrix with a higher content of glycosaminoglycans than corresponding native tissues. Thus, extracellular matrix synthesized during culture contains high quantities of glycosaminoglycans and is consequently more "watery" than native tissues. Hence, engineered tissues are ideal for the production and isolation of glycosaminoglycans, which bind water and confer tissue turgor to connective tissues.

To produce isolated human glycosaminoglycans, human vascular cells are cultured in medium containing high serum (i.e. >10% by volume of serum), and after several weeks, tissues are removed from culture and treated with hyaluronidase or other glycosaminoglycan-cleaving enzymes. Supernatant from this digestion is collected, containing high molecular weight glycosaminoglycans that may be isolated using dialysis, centrifugation, or other techniques known in the art. These glycosaminoglycans may then be used to confer tissue turgor to a treated area.

In addition to the methods described above, human glycosaminoglycans and human hyaluronic acid may be derived from native vascular tissues. Native human blood vessels are treated with a protease such as pepsin or collagenase, in order to break up confining, fibrillar extracellular matrix. Preferably, the native blood vessels are extracted from discarded human umbilical cords. Such protease pre-treatment exposes glycosaminoglycans and hyaluronans to aqueous solution and allows swelling. Glycosaminoglycans and hyaluronans may then be collected from vascular tissues by any of a variety of techniques known in the art, including treatment with hyaluronidase, detergent treatment, or treatment with other enzymes that cleave glycosaminoglycan moieties.

The supernatant collected from this treatment can then be purified for high molecular weight glycosaminoglycans by any of a variety of methods, including dialysis, centrifugation, immune isolation and precipitation, etc. Preferably, the glycosaminoglycans have a MW greater than 100,000 kDa.

Additional Active Agents

The compositions of the present invention may also include an effective amount of one or more active agents and a pharmaceutically acceptable carrier. In some embodiments, it may be useful to include one or more anti-inflammatory agents, tissue formation agents, anesthetics, antioxidants and the like, or combinations thereof.

Anti-inflammatory agents can include, but are not limited to, naproxen, sulindac, tolmetin, ketorolac, celecoxib, ibuprofen, diclofenac, acetylsalicylic acid, nabumetone, etodolac, indomethacin, piroxicam, cox-2 inhibitors, ketoprofen, antiplatelet medications, salsalate, valdecoxib, oxaprozin, diflunisal, flurbiprofen, corticosteroids, MMP inhibitors and leukotriene modifiers or combinations thereof.

Agents that increase formation of new tissues at the site of application can include, but are not limited to, fibroblast growth factor (FGF), transforming growth factor-beta (TGF-β), platelet-derived growth factor (PDGF) and/or fragments of angiotensin II (A-II) or combinations thereof.

Anesthetics can include, but are not limited to, those used in caudal, epidural, inhalation, injectable, retrobulbar, and spinal applications, such as bupivacaine, lidocaine, benzocaine, cetacaine, ropivacaine, and tetracaine, or combinations thereof.

Antioxidants can include, but are not limited to, Vitamin C, Vitamin A, Vitamin E, β-carotene, superoxide dismutase, catalase, selenoenzyme glutathione peroxidase, ubiquinones/ubiquinols, thioredoxin reductase, propyl, octyl and dodecyl esters of gallic acid, butylated hydroxyanisole (BHA), butylated hydroxytoluene (BHT) and nordihydroguaiaretic acid or combinations thereof.

Compositions used in the invention may additionally include one or more biologically active agents to aid in the healing or regrowth of natural tissue. For example, one may incorporate factors such as heparin, connective tissue activating peptides, β-thromboglobulin, insulin-like growth factors, tumor necrosis factors, interleukins, colony stimulating factors, erythropoietin, nerve growth factors, interferons, osteogenic factors including bone morphogenic proteins, and the like.

Any drug or other agent which is compatible with the compositions and methods of manufacture may be used with the present invention. Decisions to use such drug or agent are typically made by the attending physician based on judgments about the injury or defect being repaired.

Methods of Isolating and Purifying Extracellular Matrix Proteins

There are numerous art recognized techniques that can be used to extract extracellular matrix components from native and engineered tissues. Specific enzymes that may be used to extract collagen and elastin matrix components include, but are not limited to, collagenase; pepsin; trypsin; elastase; matrix metalloproteinases; dispase; serine proteases; other suitable proteases; high concentrations of salts such as NaCl or other salts; alkali treatment; acid treatment; Heat (for example, autoclaving, boiling, or baking); detergents (for example, SDS or CHAPS) and/or hypotonic treatment, (for example, water) or combinations of these treatments.

There are numerous art recognized techniques that can be used to isolate and purify the extracellular matrix components that are extracted from the engineered or native vascular tissues. Such methods may include, but are not limited to, centrifugation; salt precipitation of proteins such as collagen; immunoprecipitation; antibody-mediated binding to beads followed by cleavage to isolate matrix component; isolation based upon hydrophobicity/hydrophilicity (for example, extracting hydrophobic elastin by adhesion to hydrophobic substrate such as polystyrene); dialysis (to remove low molecular weight contaminants, enzymes, salt, acid, for example); drying; altering pH of solution to induce precipitation of extracellular components; inactivation of enzymes that were used for isolation; and/or chromatographic methods (for example, polyacrylamide gel electrophoresis or high performance liquid chromatography that separate components based upon charge and molecular weight); or combinations of these treatments.

There are numerous art recognized techniques that can be used to decellularize engineered or native tissues prior to extracellular matrix isolation, in order to increase the purity of the extracted matrix, enhance its biocompatibility and persistence in vivo, and to ease the isolation of selected matrix components. In one example, aqueous hypotonic or low ionic strength solutions facilitate cell lysis in engineered and native tissues through osmotic effects. Such solutions may comprise deionized water or an aqueous hypotonic buffer (e.g., at a pH of approximately 5.5 to 8, preferably approximately 7 to 7.5). Decellularization may be accomplished using a single decellularization solution, or the construct may be incubated sequentially in two or more solutions. Another approach involves immersing the construct in alternating hypertonic and hypotonic solutions.

Preferred decellularization agents include, but are not limited to, salts, detergent/emulsification agents and enzymes such as proteases, and/or nucleases. Combinations of different classes of detergents, e.g., a nonionic detergent such as Triton X-100 (tert-octylphenylpolyoxyethylene) and an ionic detergent such as SDS (sodium dodecyl sulfate) may be employed. Preferably, one or more decellularization solutions include Triton X-100, CHAPS (3-[(3-cholamidopropyl)-dimethyl-ammonio]-1-propanesulfonate), or SDS in phosphate buffered saline (PBS). Other suitable detergents include polyoxyethylene (20) sorbitan mono-oleate and polyoxyethylene (80) sorbitan mono-oleate (Tween 20 and 80), sodium deoxycholate, and octyl-glucoside. In certain preferred embodiments, various additives such as metal ion chelators, e.g., EDTA (ethylenediaminetetraacetic acid) and/or protease inhibitors are included in the decellularization solution. Suitable protease inhibitors for use in decellularization solutions include, but are not limited to, one or more of the following: phenylmethylsulfonyl-fluoride (PMSF), aprotinin, leupeptin, and N-ethylmaleimide (NEM).

Various enzymes that degrade cellular components may be included in the decellularization solution. Such enzymes include nucleases (e.g., DNAses such as DNAse I, RNAses such as RNAse A), and phospholipases (e.g., phospholipase A or C). Certain proteases such as dispase II, trypsin, and thermolysin may be of use in decellularization. The decellularization solution preferably includes a buffer. In general, a pH between about 5.5 and 8.0, preferably between about 6.0 and 7.8, more preferably between about 7.0 and 7.5 is employed. Preferred buffers include organic buffers such as Tris (hydroxymethyl) aminomethane (TRIS), (N-[2-hydroxyethyl] piperazine-N-[2-ethanesulfonic acid] (HEPES), etc. Buffers including sodium phosphate, citrate, bicarbonate, acetate, or glutamate may also be used.

Physical forces such as the formation of intracellular ice may be employed as a primary means of accomplishing decellularization or to augment the activity of decellularization solutions. One such approach referred to as vapor phase freezing involves placing the construct or tissue in an appropriate solution, e.g., a standard cryopreservation solution such as Dulbecco's Modified Eagle Medium (DMEM), 10% dimethylsulfoxide (DMSO), 10% fetal bovine serum (FBS) and cooling at a slow rate, e.g., 1-2° C. Multiple freeze-thaw cycles may be employed. Colloid-forming materials may be added to the solution to reduce extracellular ice formation while allowing formation of intracellular ice. Appropriate materials include polyvinylpyrrolidone (10% w/v) and dialyzed hydroxyethyl starch (10% w/v).

Pharmaceutical Compositions and Modes of Administration

The compounds of the present invention are administered to a patient in the form of a pharmaceutical composition. A compound that is administered in a pharmaceutical composition is mixed with a pharmaceutically acceptable carrier or excipient such that a therapeutically effective amount is present in the composition.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

The terms "effective amount" or "therapeutically effective amount" refers to an amount of the compound that is nontoxic and necessary to achieve a desired endpoint or therapeutic effect (e.g., act as a dermal or subdermal filler).

A variety of preparations can be used to formulate the compositions or active agents of the present invention to render the most appropriate pharmaceutical compositions. Techniques for formulation and administration may be found in "Remington: The Science and Practice of Pharmacy, Twentieth Edition," Lippincott Williams & Wilkins, Philadelphia, Pa. For human administration, preparations should meet sterility, pyrogenicity, general safety and purity standards as required by the FDA. Administration of the pharmaceutical composition can be performed in a variety of ways, as described herein.

The active agent may be administered, if desired, in the form of a salt, ester, amide, prodrug, derivative, or the like, provided the salt, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992).

The amount of active agent (e.g., collagen, elastin, etc.) administered will depend on a number of factors and will vary from subject to subject and depend on the particular drug administered, the particular disorder or condition being treated, the severity of the symptoms, the subject's age, weight and general condition, and the judgment of the prescribing physician. The minimum amount of drug is determined by the requirement that sufficient quantities of drug must be present in a device or composition to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

The term "dosage form" denotes any form of a pharmaceutical composition that contains an amount of active agent sufficient to achieve a therapeutic effect with a single administration. When the formulation is an injection, the dosage form is usually one such injection. The frequency of administration that will provide the most effective results in an efficient manner without overdosing will vary with the characteristics of the particular active agent, including both its pharmacological characteristics and its physical characteristics.

The compositions of the present invention can also be formulated for controlled release or sustained release. The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period.

The present formulations may also include conventional additives such as opacifiers, colorants, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Administration of a compound of the invention may be carried out using any appropriate mode of administration. Thus, administration can be, for example, oral, parenteral, topical, transdermal, transmucosal (including rectal and vaginal), sublingual, by inhalation, or via an implanted reservoir in a dosage form.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995).

The dose regimen will depend on a number of factors that may readily be determined, such as severity of the condition and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies, and repetition rates. In general, it is contemplated that the formulation will be applied one to four times daily. With a skin patch, the device is generally maintained in place on the body surface throughout a drug delivery period, typically in the range of 8 to 72 hours, and replaced as necessary.

Preferably, the pharmaceutical compositions of the present invention can be administered parenterally to a subject/patient in need of such treatment. The term "parenteral" as used herein is intended to include subcutaneous (dermal or subdermal), intravenous, and intramuscular injection or implantation (e.g., subcutaneously or intramuscularly or by intramuscular injection).

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

A carrier for parenteral administration can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. It is also advantageous to include one or more cells or tissues which may supplement the use of the composition of the present invention. For example, it is preferred to include adipose tissue or cells, dermal fibroblasts or combination of thereof.

Suitable preservatives for use in solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The compositions of the invention can be formulated for parenteral administration by dissolving, suspending or emulsifying in an aqueous or nonaqueous solvent. Vegetable (e.g., sesame oil, peanut oil) or similar oils, synthetic aliphatic acid glycerides, esters of higher aliphatic acids and propylene glycol are examples of nonaqueous solvents. Aqueous solutions such as Hank's solution, Ringer's solution or physiological saline buffer can also be used. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for subcutaneous or intramuscular injection is also contemplated. In this regard, the use of DMSO as solvent is preferred as this will result in extremely rapid penetration, delivering high concentrations of the active compound(s) or agent(s) to a small area.

The present invention also provides kits for performing soft tissue augmentation. Such kits can be prepared from readily available materials and reagents and can come in a variety of embodiments. For example, such kits can comprise, in an amount sufficient for at least one treatment, any one or more of the following materials: human elastin and collagen isolated by methods of the present invention, sterilized buffers (e.g., phosphate buffered salt) or water, other reagents necessary or helpful to perform the method, and instructions. Typically, instructions include a tangible expression describing reagent concentration or at least one method parameter, such as the amount of reagent to be used, maintenance time periods for reagents, and the like, to allow the user to carry out the methods described above. In a preferred embodiment of the invention, a kit comprises a means for delivery. Such means can include, by way of illustration and not limitation, a small syringe (22 to 27-gauge), a large syringe (13 to 19-gauge) and equipment used in endoscopic or percutaneous discectomy procedures. The reagents can be provided in solution, as suspensions, or as a substantially dry powder, e.g., in lyophilized form, either independently or in a mixture of components to improve ease of use. Where a degradable reagent is provided, conditions are chosen so as to stabilize the reagent, e.g., storage at lower temperature, addition of stabilizing agents (e.g., glycerol or a reducing agent). Unstable reagents can be provided together with or separately from the more stable components of the kit.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The present invention is further illustrated by the following examples that should not be construed as limiting in any way.

EXAMPLES

Example 1

Isolation of Collagen from Engineered Vascular Tissue

Vascular tissues are engineered from human vascular smooth muscle cells according to methods as previously described (Niklason et al., Science 284(5413):489-93, 1999). Briefly, vascular smooth muscle cells from screened and banked human vascular cell sources are seeded onto a tubular synthetic fibrous scaffolding comprising polyglycolic acid fibers. The tubular seeded scaffold is threaded over distensible silicone tubing within a sterile bioreactor. The bioreactor is filled with culture medium that supports the synthesis of collagen by vascular cells. Specifically, this medium comprises Dulbecco's Modified Eagles Medium (DMEM) supplemented with 20% fetal bovine serum or other serum, ascorbic acid (50 mg/L), growth factors such as platelet derived growth factor (10 ng/mL), basic fibroblast growth factor (10 ng/mL), epidermal growth factor (3 ng/mL), proline 50 mg/L, glycine 50 mg/L, alanine 20 mg/L, copper sulfate 3 ng/mL. Other medium components that support growth of cells and/or extracellular matrix production may also be included in the culture medium. Cyclic pulsatile radial strain may be administered to the tubular constructs over the silicone tubing by pumping fluid through the tubing, with distensions of 1-5% being most preferable. Alternatively, cyclic strain may be omitted during culture, in order to simplify the culture system. Culture is maintained for 2-10 weeks, during which time collagenous matrix is synthesized by the vascular smooth muscle cells.

At the conclusion of culture, the engineered vascular tissue is decellularized using techniques similar to those reported in the art (Dahl, Cell Transplant 12(6):659-66, 2003). Specifically, detergent-based decellularization can incorporate two different treatment solutions. Solution 1 includes 8 mM CHAPS, 1.0 M NaCl, and 25 mM EDTA in PBS. Engineered vascular tissues are exposed to this solution for one hour. Following rinses in PBS, engineered vascular tissues are then exposed to Solution 2 for one hour. Solution 2 includes 1.8 mM sodium dodecyl sulfate, 1.0 M NaCl, and 25 mM EDTA in PBS. Engineered vessels are then rinsed in PBS and are rendered acellular by this process. All treatments are performed at room temperature or at about 37° C.

The following steps are used to isolate and purify the collagen from the decellularized, engineered human vascular tissues:

1. Begin with a celluar engineered material. Cut, slice, blend, chop into small pieces.

2. Digest tissue material in pepsin (0.5 to 2.0 mg/ml pepsin concentration dissolved in a low pH solution) at 4-20° C. Agitation during digest will aid the process.

3. Once digestion has completed, centrifuge briefly to remove any undigested material.

4. Remove supernatant and raise the pH of the solution to about pH 8.5 by slowly adding NaOH to inactivate pepsin.

5. Using HCl, bring the pH of the solution back to about pH 3.5.

6. Clarify collagen solution using diatomaceous earth.

7. Precipitate clarified collagen by adding NaCl to the solution. Precipitate at 4° C. for >24 hrs.

8. Collect precipitated collagen by chilled centrifugation at high speeds for ~30 minutes.

9. Aspirate supernatant carefully and resuspend precipitated collagens in ice-cold HCl. Allow for collagen molecules to completely solubilized.

10. Dialyze solution to further purify collagen.

11. Concentrate collagen to desired level.

12. Store this purified collagen in solution.

13. Add sterile-filtered sodium diphosphate solution to concentrated, purified, collagen, until final concentration of about 20-50 mM and about pH 7.4 is reached. Incubate at 22-37° C. for >24 hours.

14. An opaque white fibrous precipitate will form, containing large macromolecular collagen fibrils.

15. Centrifuge to obtain the resulting high concentration of fibrillar collagen for injection, discarding supernatant.

Using these steps, collagen is extracted from engineered, decellularized tissues. Extracted collagen is then run on a polyacrylamide gel to assess preservation of chain morphology and purity. FIG. 1 shows the very high levels of collagen purity in this preparation, as compared to the purified bovine collagen control. Hence, the methods in this example produce highly pure, collagen from engineered vascular tissues.

Example 2

Isolation of Elastin from Engineered Vascular Tissue

Synthesis of cross-linked, insoluble elastin in cultured cells is typically quite difficult. While many reports exist of synthesis of non-crosslinked tropoelastin monomers, creation of documented, cross-linked elastin is extremely rare. Most reports of production of insoluble elastin utilize cells that have been genetically engineered, for example to express high levels of tropolelastin protein, or to express variants of versican that stimulate elastin deposition. Alternatively, rodent cells derived from neonatal animals have been reported to synthesize elastin. However, non-human elastin is associated with risks of immune rejection if injected into a human recipient. Further, utilizing genetically modified cells to generate human elastin carries intrinsic risks of passing on transgene material to any eventual recipient of the extracellular matrix material.

Hence, it is advantageous to devise methods to generate crosslinked, insoluble elastin from cultured human cells, without the use of genetic engineering. In particular, the use of human vascular cells that are banked and have been screened for infectious agents also helps to reduce any infectious risk of resultant elastin that is produced.

The methods of the present invention culture human vascular tissues to produce measurable amounts of insoluble, crosslinked elastin, as indicated by desmosine analysis. Such tissues may then be decellularized and the elastin within these tissues extracted and purified. In one example, human vascular smooth muscle cells are seeded onto polyglycolic acid scaffolds in bioreactors, analogously to the procedure described in Example 1. Cyclic strain may be applied via the luminal silicone tubing, or may be omitted, in order to simplify the culture conditions. Total culture time may vary from 2-10 weeks. In this example, total culture time is 3 weeks. Culture medium that is designed to stimulate elastin synthesis for the first two weeks of culture contains the following components:

1. 400 mL DMEM-low glucose
2. 100 mL Human Serum
3. 5 mL (50,000 U) of Penicillin G
4. 2.5 mg Insulin,
5. 0.5 µg $CuSO_4$ 6. 5 ml aliquot of Glycine/Alanine/Valine/Proline (30 mg/18 mg/17.5 mg/11.5 mg)
7. Dexamethasone $10^{-8}$-$10^{-10}$ M
8. 2.5 µg TGF-beta In order to further stimulate elastin synthesis by cultured human vascular smooth muscle cells within the engineered tissue, the following medium is used during the final week of culture:

1. 475 mL DMEM-low glucose
2. 25 mL Human Serum
3. 5 mL (50,000 U) of Penicillin G
4. 2.5 mg Insulin, (5 µg/ml)
5. 1.5 µg $CuSO_4$
6. 5 ml aliquot of Glycine/Alanine/Valine/Proline (30 mg/18 mg/17.5 mg/11.5 mg)
7. Dexamethasone $10^{-8}$-$10^{-10}$ M
8. 2.5 µg TGF-beta (5 ng/mL)

Using these culture conditions, engineered vascular tissues containing elastin, cells and other matrix components are generated. At the conclusion of culture, engineered vascular tissues are subjected to the decellularization process as described in Example 1. Subsequent to this decellularization process, the intact and decellularized tissues are subjected to analysis for desmosine, which is a covalent cross-link component in mature elastin. Presence of desmosine indicates the production of mature elastin by engineered vascular tissues. Table 1 contains desmosine results for a variety of engineered vascular tissues, both intact and decellularized.

TABLE 1

| Samples | pmol Desmosine/mg Protein | pmol Desmosine/mg Tissue |
|---|---|---|
| Fresh-1 | 32 | 25 |
| Fresh-2 | 29 | 27 |
| Fresh-3 | 37 | 20 |
| Fresh-4 | 49 | 35 |
| Fresh-5 | 57 | 26 |
| Fresh-6 | 67 | 29 |
| Fresh-7 | 41 | 12 |
| Decellutarized-1 | 53 | 29 |
| Decellutarized-2 | 31 | 34 |
| Decellutarized-3 | 39 | 19 |
| Decellutarized-4 | 55 | 46 |
| Decellutarized-5 | 37 | 25 |
| Decellutarized-6 | 28 | 35 |
| Decellutarized-7 | 64 | 51 |

Table 1 shows that desmosine elastin cross-links are present in intact engineered tissues, and are retained after the decellularization process. Hence, it is feasible to engineer cross-linked elastin that is stable following removal of cellular constituents. Isolation of elastin from engineered and decellularized vascular tissues may then be accomplished by any one of several methods known in the art, including, but not limited to, autoclaving, alkali or acid treatment, pepsin or collagenase digestion, or combinations of these treatments.

Example 3

Isolation of Elastin from Native Human Umbilical Vessels

Elastin is isolated from native human blood vessels, such as those isolated from discarded umbilical cords. Vessels are decellularized and then elastin is isolated from the resultant extracellular matrix. The solutions for decellularization process are those described in Example 1. Steps used in the decellularization and elastin isolation process are as follows:

1. Thaw frozen umbilical artery or vein overnight at 4° C.
2. Record vessel length and weight.
3. Decellularize vessel in Solution 1 for 12 hr.
4. Rinse 2 times with phosphate buffered saline, 5 min each.
5. Decellularize in Solution 2 for 12 hr.
6. Rinse 3 times with phosphate buffered saline, 5 min each.

Digest decellularized umbilical artery or vein with pepsin or collagenase at 37° C. or room temperature for 1-5 hr with gentle shaking. This removes non-elastin extracellular matrix components.

7. Alternatively, decellularized vessels may be autoclaved for 3-4 cycles at 121° C. for 30 min or 115° C. for 20 min, to remove non-elastin extracellular matrix components.
8. Rinse digested tissue or autoclaved tissue with distilled water.
9. Snap freeze tissue in dry ice.
10. Lyophilize tissue overnight.
11. Subject resultant elastin to amino acid analysis to evaluate purity.
12. Further digest the purified elastin with pepsin to produce injectable particle size.
13. Alternatively, mechanically break down elastin using mortar/pestle or a mill or homogenizer, to produce particles of a size appropriate for injectable products, preferably less than about 200 μm, more preferably less than about 100 μm, most preferably less than about 50 μm.

Human umbilical vessels are treated according to the steps in this example, and are analyzed for amino acid content to determine elastin purity (step 12 above). Table 2 indicates the exact preparation steps from the above list that are used for each sample.

TABLE 2

| Samples | 1 | 2 | 3 | 4 | 5 | 6 | 7 | 8 |
|---|---|---|---|---|---|---|---|---|
| NaCl extraction | y | | | | y | | | |
| Autoclave | | 115C | 115C | 115C | 115C | 121C | 121 | |
| Delipid | Y | y | y | y | y | y | | |
| decell | | | | | | y | y | y |
| Pepsin | | | | | | | 37C | RT |

Table 3 shows results of the amino acid analysis of the resultant purified elastins.

TABLE 3

| | Sample # | | | | | | | | Expect- |
|---|---|---|---|---|---|---|---|---|---|
| | 1 | 2 | 3 | 4 | 5 | 6 | 7 | 8 | ed |
| *CVS | 16 | 0 | 24 | 2 | 23 | 3 | 0 | 0 | 3 |
| asx | 93 | 73 | 92 | 88 | 96 | 38 | 94 | 79 | 2 |
| thr | 38 | 23 | 45 | 42 | 43 | 21 | 38 | 28 | 14 |
| ser | 31 | 24 | 34 | 31 | 34 | 13 | 37 | 30 | 9 |
| glx | 111 | 98 | 120 | 116 | 125 | 51 | 100 | 88 | 3 |
| pro | 87 | 104 | 76 | 84 | 68 | 113 | 94 | 144 | 129 |
| gly | 202 | 352 | 145 | 157 | 134 | 286 | 273 | 326 | 312 |
| ala | 96 | 120 | 100 | 107 | 99 | 197 | 97 | 110 | 239 |
| val | 73 | 37 | 76 | 81 | 78 | 123 | 55 | 41 | 137 |
| *met | 6 | 0 | 5 | 14 | 0 | 0 | 0 | 0 | 0 |
| ile | 44 | 24 | 48 | 53 | 50 | 31 | 52 | 28 | 24 |
| leu | 76 | 40 | 85 | 84 | 88 | 66 | 69 | 45 | 65 |
| *tyr | 0 | 0 | 3 | 2 | 0 | 0 | 0 | 0 | 23 |
| phe | 28 | 15 | 33 | 34 | 35 | 26 | 29 | 20 | 24 |
| his | 1 | 0 | 8 | 6 | 23 | 0 | 0 | 0 | 0 |
| lys | 50 | 36 | 60 | 57 | 59 | 25 | 33 | 29 | 9 |
| arg | 47 | 54 | 46 | 43 | 44 | 8 | 30 | 32 | 9 |

Values are Residues/1000

In Table 3, the "Expected" column indicates the number of amino acid residues per 1000 amino acid residues that would be expected in the case of completely pure human elastin. It is clear from Table 3 that Sample 6 contains the most highly pure isolated elastin. This sample was prepared using decellularization and autoclave extraction (see Table 2). Hence, in contrast to previously reported techniques that claim to isolate pure elastin from other types of tissues, it had been found that human vascular tissues require an additional decellularization step in order to isolate elastin of sufficient purity. This finding is in contrast to multiple reports in the literature that claim that autoclave treatment alone, when applied to other tissues such as bovine ligamentum nuchae, produces a highly pure elastin preparation (Lee et al., American Journal of Pathology 2006; 168: 490-498). From Table 3, it is clear that standard methods such as autoclaving, without an additional decellularization step, produce highly impure elastin products when applied to native human umbilical cord vascular material.

Example 4

Isolation of Elastin from Native Human Aorta

Elastin is also purified from human aorta. The process involves a salt-based decellularization step, followed by boiling in 0.1 N NaOH and then extraction in hydrophobic solvents. Elastin isolation according to this example has unexpected properties when implanted in vivo, as shown in Example 5 (below). Steps for purifying elastin from aorta according to the present invention are as follows:

1. Obtain wet weight of aorta. Aorta is preferably fresh or non-frozen.
2. Shred aorta using a blender or some other device in distilled water.
3. Extract shredded tissues at 1-hour intervals in 0.9% NaCl solution at 4° C. with shaking.
4. Repeat NaCl extraction until protein assay shows no soluble protein extraction.
5. Suspend samples in boiling 0.1 N NaOH solution, boil for 40-45 minutes.
6. Discard NaOH solution, then rinse with distilled water.
7. Extract elastin 3 times, 30 minutes each, with 100% ethanol at room temperature.
8. Extract elastin in 50% ethanol/50% diethyl ether for 1 hour at room temperature.
9. Extract elastin in 100% diethyl ether for 1 hour at room temperature.
10. Decant ether, dry overnight. Obtain final weight.
11. Grind or pulverize to create injectable and insoluble elastin particles.

The amino acid analysis is performed, along with the RIA analysis for desmosine cross-links, of elastin that is purified from human aorta using the above method. For these experiments, a total of 6 different aortas are treated using this protocol, and amino acid analysis is performed on 4 of the 6 samples. Desmosine quantification is performed on all samples as summarized in Table 4.

TABLE 4

AA analysis and Desmosine for elastin from human aorta:
(per 1.000 total residues)

| Amino Acid | Sample 54 | Sample 55 | Sample 56 | Sample 57 | Expected |
|---|---|---|---|---|---|
| *cys | 0 | 0 |  |  | 3 |
| asx | 7 | 7 | 5 | 6 | 2 |
| thr | 9 | 8 | 5 | 5 | 14 |
| ser | 6 | 6 | 3 | 3 | 9 |
| glx | 21 | 21 | 20 | 19 | 3 |
| pro | 116 | 116 | 111 | 111 | 129 |
| gly | 332 | 331 | 353 | 353 | 312 |
| ala | 263 | 263 | 261 | 259 | 239 |
| val | 114 | 116 | 127 | 127 | 137 |
| *met | 0 | 0 | 0 | 0 | 0 |
| ile | 23 | 25 | 21 | 21 | 24 |
| leu | 60 | 61 | 55 | 58 | 65 |
| *tyr | 13 | 14 | 5 | 3 | 23 |
| phe | 24 | 25 | 19 | 21 | 24 |
| his | 0 | 0 | 0 | 0 | 0 |
| lys | 6 | 7 | 11 | 9 | 9 |
| arg | 5 | 4 | 5 | 5 | 9 |
| Des (pM/mg) | 12332 | 13291 | 19793 | 11904 |  |

*Cys, Tyr and Met are partially destroyed during acid hydrolysis
Desmosine units are in (pico Moles/mg Protein)

As shown in Table 4, the values of alanine are well above 200 residues per 1,000 total residues, and values of valine are well above 70 residues per 1,000 residues. These are consistent with high purity elastin protein. In addition, values of Desmosine cross-links are very high, and are comparable to or higher than those reported for elastin preparations from a variety of species (see Table 5):

TABLE 5

Desmosine from aortas of different species (pM/mg protein)
picomole/mg protein

| | |
|---|---|
| Cow | 12573 |
| Pig | 13934 |
| Monkey | 10948 |
| Rat | 6266 |
| Dog | 12942 |

Figure 2:
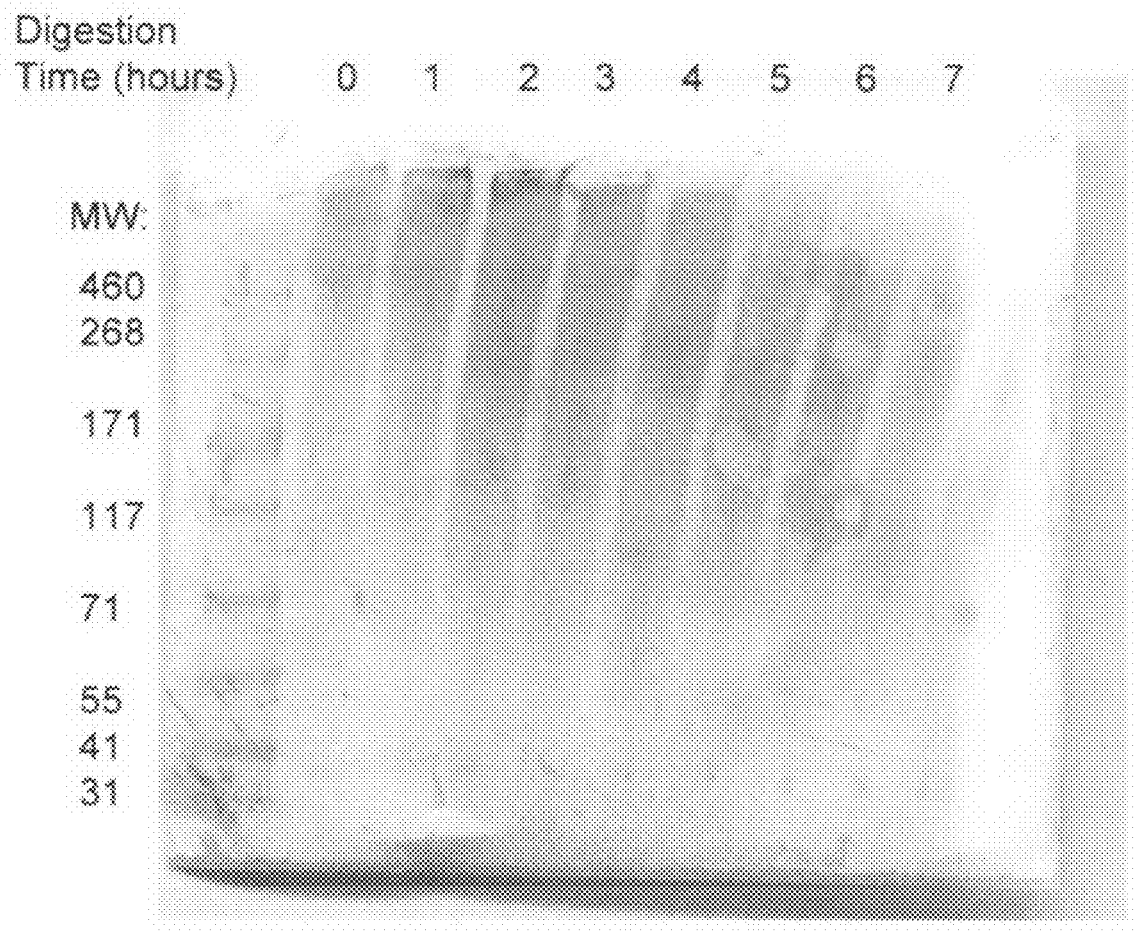
FIG. 2 illustrates the results of a polyacrylamide gel showing immunoreactivity of isolated proteins with elastin antibody, showing that elastin is isolated having molecular weights in the range of approximately 100 kDa or greater.

An alternative method in accordance with the present invention is to isolate elastin from human aorta using a pepsin digestion. FIG. 2 shows an immunoblot of proteins isolated from human aorta using pepsin digestion, and reacted with anti-elastin antibody. For digestion times ranging from 2-5 hours, extensive protein is liberated that reacts with elastin antibody, having molecular weights (MW) in the approximate range of 100-500 kDa (i.e., greater than 100 kDa).

Example 5

Implantation of Purified Elastin In vivo

One drawback of other elastin preparations is a tendency to calcify in vivo. Implantation into juvenile (i.e. 21 day-old) rats is an extremely sensitive assay for calcification. In order to determine the propensity of human elastin that is isolated according to the present invention to calcify, the elastin was implanted subdermally into rats. The human elastin was isolated from aorta according to the present invention using salt-based decellularization followed by NaOH extraction as described in Example 4. Calcification was compared to that induced by purified bovine elastin (purchased commercially), syngeneic rat aorta (containing rat elastin), and injection of phosphate buffered saline control. Implants remained in situ for 21 days and then were explanted. Calcification was assessed histologically, using the alizarin red stain, which produces a reddish-brown color in calcified tissues. In addition, calcium accumulation at implant sites was determined quantitatively by atomic absorption spectroscopy.

Figure 3:
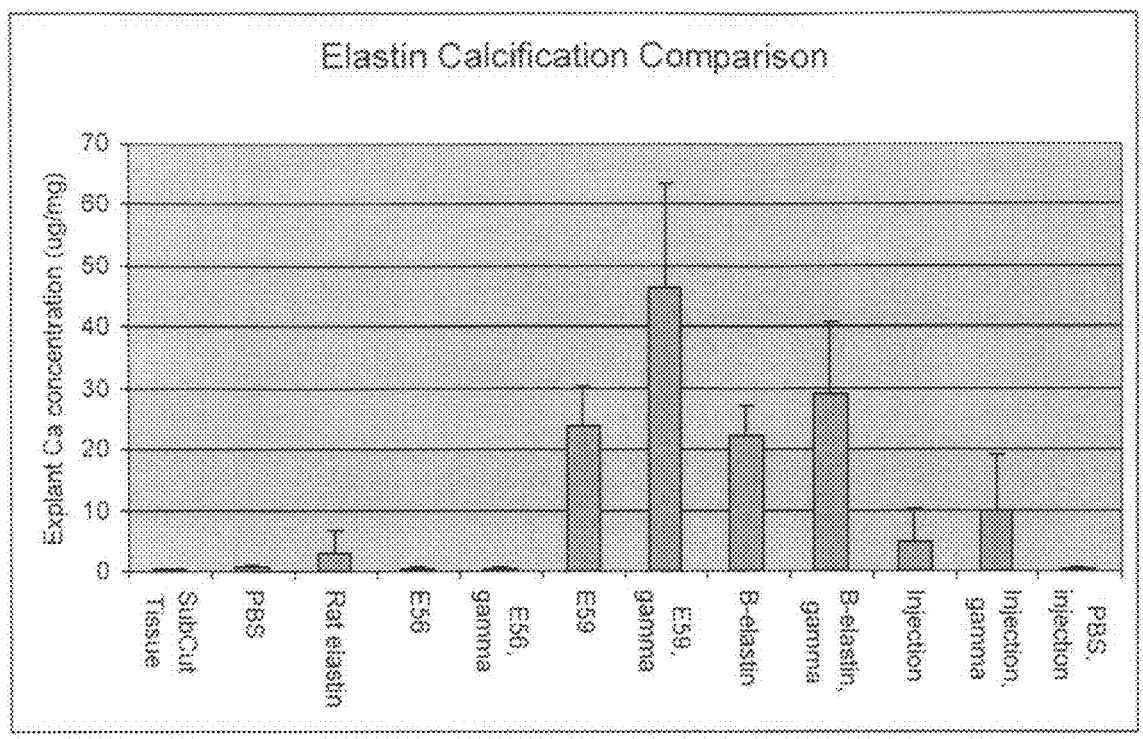
FIG. 3 illustrates the low degree of calcification of implanted elastin preparations in a juvenile rat model showing that elastin isolated according to the present invention results in calcification levels that are indistinguishable from vehicle control.

FIG. 3 shows the atomic absorption spectroscopy of calcium content of explanted tissues from juvenile rats that contained various elastin implants or control implants. Error bars are standard deviation of the mean. Various samples were analyzed: juvenile rat subcutaneous tissue, negative control (SubCut Tissue); phosphate buffered saline carrier (PBS); syngeneic rat aorta, containing syngeneic rat elastin (Rat Elastin); human elastin isolated according to the present invention, from fresh aorta (E56); human elastin isolated according to the present invention, from fresh aorta, sterilized by gamma radiation (E56 gamma); human elastin isolated according to the present invention, from frozen aorta (E59); human elastin isolated according to the present invention, from frozen aorta, sterilized by gamma radiation (E59 gamma); purified bovine elastin obtained from Elastin Products Co. (B-elastin); purified bovine elastin from Elastin Products Co, sterilized by gamma radiation (B-elastin gamma); injectable form of bovine elastin obtained from Elastin Products Co. (B-elastin Injection); injectable form of bovine elastin obtained from Elastin Products Co, sterilized by gamma radiation (Injection B-elastin Gamma); and phosphate buffered saline carrier (Injection PBS)

The results of atomic absorption spectroscopy show that calcium levels in explants having elastin that is isolated from non-frozen human aorta according to the present invention are not different from calcium levels in tissues that are injected with PBS carrier. However, the results show that when elastin was isolated according to the present invention from frozen aorta, tissue calcification was significantly increased. Overall, there does not appear to be any impact of sterilization by gamma irradiation on the degree of tissue calcification for any of the forms of elastin that is tested (see FIG. 3 for the atomic absorption spectroscopy results and Table 6 for summary of the corresponding quantitative values of calcium in tissue explants)

Figure 4:
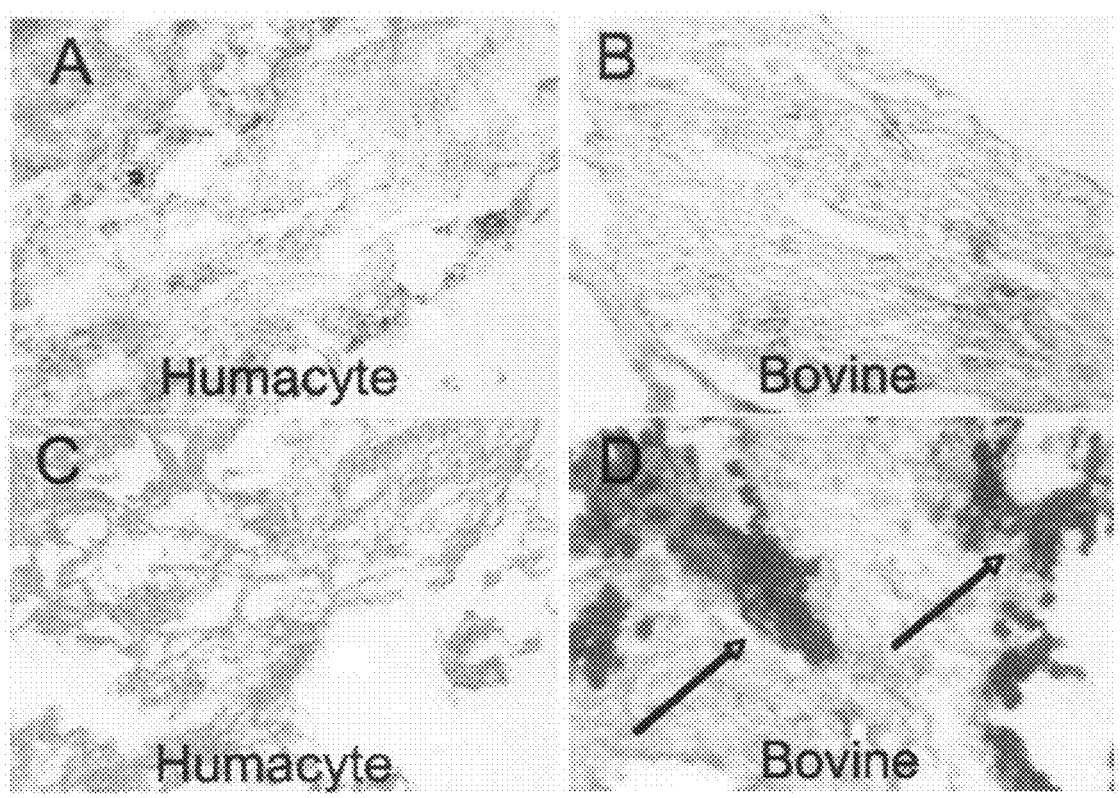
FIG. 4 H&E and alizarin red staining of elastin compared to commercial, purified bovine elastin, implanted into juvenile rats showing that calcification of elastin that is isolated according to the method of invention is negligible, while calcification of bovine elastin is extensive. Panel A and Panel B show H&E stain of explanted tissues 21 days after implantation of human elastin that was isolated according to the present invention ("Humacyte") (Panel A) and commercially obtained bovine elastin ("Bovine") (Panel B). Panel C and Panel D show alizarin red stain of explanted tissues 21 days after implantation of human elastin that was isolated according to the present invention ("Humacyte") (Panel C) and commercially obtained bovine elastin ("Bovine") (Panel D).

FIG. 4 shows the staining of explanted tissue specimens from juvenile rats implanted with elastin that was isolated according to the present invention, and with bovine elastin. A,B: Hematoxylin & eosin (H&E) stain of explanted tissues 21 days after implantation of human elastin that was isolated according to the present invention ("Humacyte") and commercially obtained bovine elastin ("Bovine"). C,D: Alizarin red stain of explanted tissues 21 days after implantation of human elastin that was isolated according to the present invention ("Humacyte") and commercially obtained bovine elastin ("Bovine"). Arrows in panel D indicate areas of visible calcification.

Figure 5:
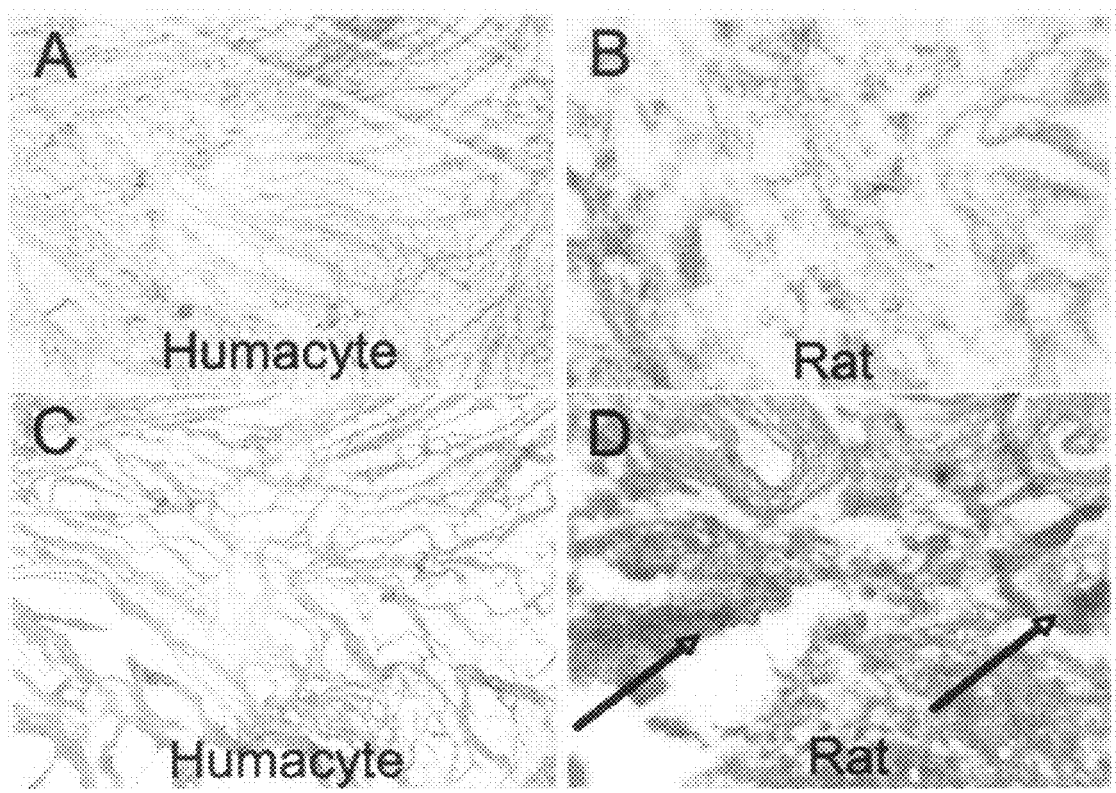
FIG. 5 illustrate the results of H&E and alizarin red staining of elastin compared to syngeneic rat aorta, implanted into juvenile rats, showing that implanted elastin calcification comparable to or less than that induced by syngeneic aorta. Panel A and Panel B show H&E stain of explanted tissues 21 days after implantation of human elastin that was isolated according to the present invention ("Humacyte") (Panel A) and syngeneic rat aorta containing elastin ("Rat") (Panel B). Panel C and Panel D show alizarin red stain of explanted tissues 21 days after implantation of human elastin that was isolated according to the present invention ("Humacyte") (Panel C) and syngeneic rat aorta containing elastin ("Rat") (Panel D).

FIG. 5 shows the staining of explanted tissue specimens from juvenile rats implanted with elastin that was isolated according to the present invention, and with syngeneic rat elastin from rat aorta. A,B: Hematoxylin & eosin (H&E) stain of explanted tissues 21 days after implantation of human elastin that was isolated according to the present invention ("Humacyte") and syngeneic rat aorta containing elastin ("Rat"). C,D: Alizarin red stain of explanted tissues 21 days after implantation of human elastin that was isolated according to the present invention ("Humacyte") and syngeneic rat aorta containing elastin ("Rat"). Arrows in panel D indicate areas of likely calcification.

Figure 6:
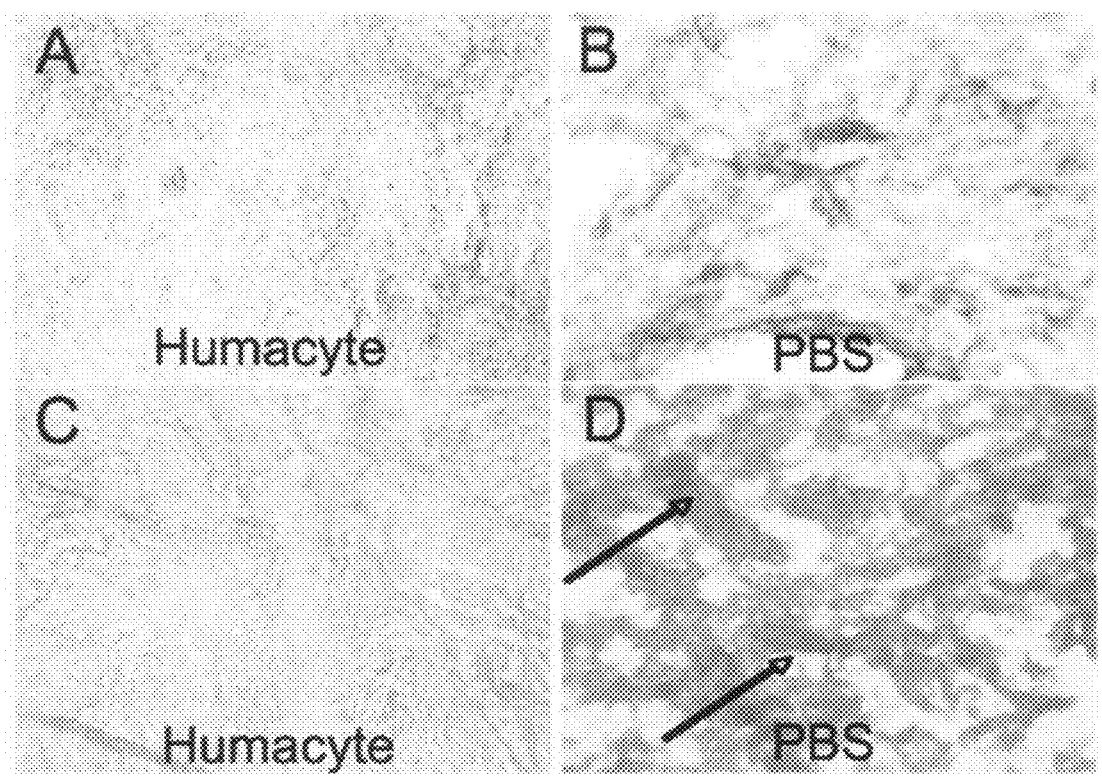
FIG. 6 illustrates the results of H&E and alizarin red staining of elastin compared to phosphate buffered saline carrier, implanted into juvenile rats showing that implanted elastin calcification is comparable to or less than that induced by saline carrier. Panel A and Panel B show H&E stain of explanted tissues 21 days after implantation of human elastin that was isolated according to the present invention ("Humacyte") (Panel A) and carrier ("PBS") (Panel B). Panel C and Panel D show alizarin red stain of explanted tissues 21 days after implantation of human elastin that was isolated according to the present invention ("Humacyte") (Panel C) and carrier ("PBS") (Panel D).

FIG. 6 shows the staining of explanted tissue specimens from juvenile rats implanted with elastin that was isolated according to the present invention, and with phosphate buffered saline carrier. A,B: Hematoxylin & eosin (H&E) stain of explanted tissues 21 days after implantation of human elastin that was isolated according to the present invention ("Humacyte") and carrier ("PBS"). C,D: Alizarin red stain of explanted tissues 21 days after implantation of human elastin that was isolated according to the present invention ("Humacyte") and carrier ("PBS"). Arrows in panel D indicate areas of possible calcification.

The H&E staining together with an alizarin red staining of explanted tissue from juvenile rats for calcification in FIGS. 4-6 confirms the results from atomic absorption spectroscopy in FIG. 3 and Table 6 regarding the degree of tissue calcification, and shows that human elastin that is isolated according to the present invention from non-frozen tissue does not induce calcification in vivo, using an extremely sensitive implantation model system.

TABLE 6

Calcium levels in explanted samples:

Calcium from Explant Tissue

| Group | Elastin source | Average | St Dev | N |
|---|---|---|---|---|
| Rat SubCut Tissue | N/A | 0.25 | 0.160421877 | 4 |
| PBS carrier | N/A | 0.49 | 0.383992568 | 6 |
| Rat elastin | Fresh aorta | 2.80 | 3.808000837 | 2 |
| E56 - Humacyte | Fresh human aorta | 0.47 | 0.195592829 | 3 |
| E - 56 Humacyte gamma | Fresh human aorta | 0.44 | 0.081904605 | 3 |
| E59-Humacyte (frozen) | Frozen human aorta | 23.73 | 6.610771334 | 3 |
| E59-Humacyte (frozen) gamma | Frozen human aorta | 46.36 | 17.10482952 | 3 |
| Bovine elastin | Elastin Products Co. | 22.26 | 4.662817486 | 6 |
| Bovine elastin, gamma | Elastin Products Co. | 28.97 | 11.63379649 | 6 |
| Bovine injectable | Elastin Products Co. | 4.76 | 5.485544335 | 4 |
| Bovine injectable, gamma | Elastin Products Co. | 9.95 | 9.181395142 | 6 |
| PBS carrier | N/A | 0.46 | 0.172634466 | 5 |

Example 6

Isolation of Human Collagen from SMCs on Micro-Carrier Beads

Human vascular smooth muscle cells can also be cultured on micro-carrier beads in a suspension culture as described herein. During the period of culturing, the smooth muscle cells replicate on the surface of the beads, and deposit collagenous extracellular matrix. The collagenous matrix is then harvested and purified according to the present invention. Specific steps in this process are as follows:

1. Culture human smooth muscle cells in a standard culture flask under conditions suitable for growth of the cells, in complete culture medium containing at least 10% serum.
2. Sterilize spinner flask by autoclaving.
3. Weigh out 2.0 g Cytodex-1 micro-carrier beads and mix with 500 mL of PBS, then sterilize by autoclaving.
4. Pipet 10 mL of micro-carrier bead slurry into spinner flask reactor.
5. Trypsinize vascular smooth muscle cells and seed onto beads in spinner flask a total of 5 million cells in 25 mL of cell growth medium.
6. Culture cells on beads in the presence of DMEM medium containing at least 10% serum, ascorbic acid (50 mg/L), growth factors such as platelet derived growth factor (10 ng/mL), basic fibroblast growth factor (10 ng/mL), epidermal growth factor (3 ng/mL), proline 50 mg/L, glycine 50 mg/L, alanine 20 mg/L, copper sulfate 3 ng/mL
7. Spin the flask at low speed, preferably not more than 10 revolutions per minute, during culture.
8. Supplement vitamin C twice per week, and replace cultures with fresh medium once per week.
9. After 4-12 weeks of culture of smooth muscle cells on beads, decant off culture medium supernatant and retain beads contains cells and collagenous matrix.
10. Digest bead and tissue material in pepsin (0.5 to 2.0 mg/ml pepsin concentration dissolved in a low pH solution) at 4-20° C. Agitation during digest will aid the process.
11. Once digestion has completed, centrifuge briefly to remove any undigested material by filtration, to remove micro-carrier beads.
12. Remove supernatant and raise the pH of the solution to about pH 8.5 by slowly adding NaOH to inactivate pepsin.
13. Using HCl, bring the pH of the solution back to about pH 3.5.
14. Clarify collagen solution using diatomaceous earth.
15. Precipitate clarified collagen by adding NaCl to the solution. Precipitate at 4° C. for >24 hrs.
16. Collect precipitated collagen by chilled centrifugation at high speeds for ~30 minutes.
17. Aspirate supernatant carefully and re-suspend precipitated collagens in ice-cold HCl. Allow for collagen molecules to completely solubilized.
18. Dialyze solution to further purify collagen.
19. Concentrate collagen to desired level.
20. Store this purified collagen in solution.
21. Add sterile-filtered sodium diphosphate solution to concentrated, purified, collagen, until final concentration of about 20-50 mM and about pH 7.4 is reached. Incubate at 22-37° C. for >24 hours.

Figure 7:
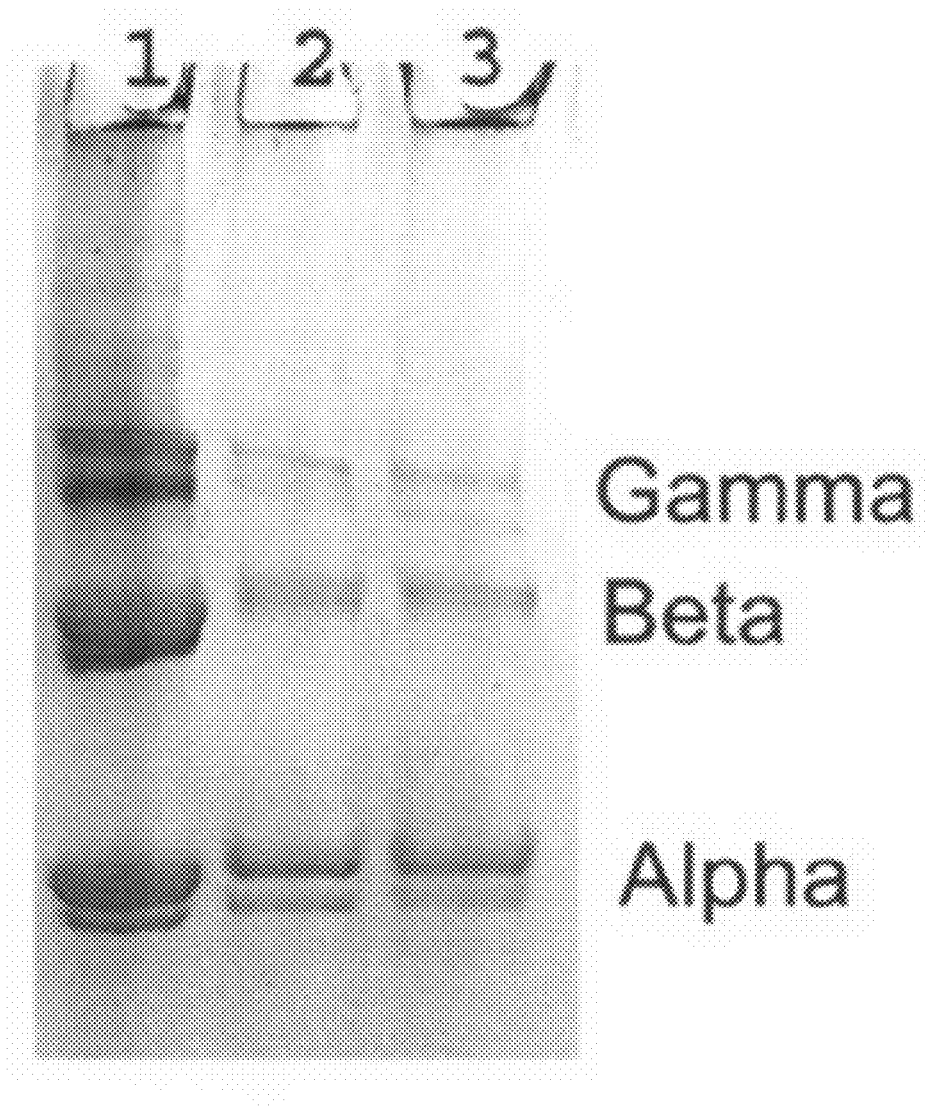
FIG. 7 illustrates the results of a polyacrylamide gel stained with comassie blue for total protein showing that human collagen isolated according to the present invention exhibit very high purity.

The purity of the resultant solubilized product produced as described herein was compared to other purified human collagens from commercial resources by polyacrylamide gel electrophoresis as shown in FIG. 7. Lane 1 shows 20 micrograms of PureCol Human Collagen, Inamed Biomaterials. Lane 2 shows 10 micrograms of collagen derived from human dermal fibroblasts. Lane 3 shows 10 micrograms of human collagen derived from vascular smooth muscle cells and purified as described in the instant example. The gel was stained with coomassie blue for protein detection. Typical collagen bands alpha, beta and gamma were present in all samples. The results in FIG. 7, Lane 3, demonstrate the high purity of collagen produced by the instant methods when compared with other samples of highly purified human collagen.

Example 7

Formulation of Injectable Collagen Material

Collagen can be formulated into an injectable product that can be delivered to patients. Soluble collagen is collected from engineered vascular tissue using the procedure contained in Example 1. Precipitated collagen is centrifuged and the supernatant removed by aspiration. The precipitated collagen is then re-suspended in a physiological saline buffer solution that is pharmaceutically acceptable (such as 0.9% sodium chloride solution) that can contain 0.3% lidocaine. The mixture is agitated to ensure uniform mixing, and pH adjusted to approximately 7.0. The volume of re-suspension solution is titrated such that the final concentration of collagen is approximately 30 mg/mL. The collagen solution is then dispensed into sterile syringes and packaged in sterile fashion, for clinical applications.

Example 8

Formulation of Injectable Collagen and Elastin Composite Material

Collagen and elastin can be combined into a composite product that is injectable. Soluble collagen is collected from engineered vascular tissue using the procedure contained in Example 1. Precipitated collagen is centrifuged and the supernatant removed by aspiration. The precipitated collagen is then re-suspended in a physiological saline buffer solution that is pharmaceutically acceptable (such as 0.9% sodium chloride solution) that can contain 0.3% lidocaine. The mixture is agitated to ensure uniform mixing, and pH adjusted to approximately 7.0. The volume of re-suspension solution is titrated such that the final concentration of collagen is approximately 20 mg/mL.

To generate the collagen-elastin composite injectable formulation, elastin is isolated from non-frozen aortic tissue according to Example 4. Insoluble elastin isolated after ether extraction is pulverized (with or without a prior freezing step to aid in particle formation) and then is sieved under sterile conditions to select particles that are less than 50 microns. Dry particles are then admixed and suspended within collagen-containing solution, in order to create the collagen-elastin composite solution. The collagen-elastin composite is then dispensed into sterile syringes and packaged in sterile fashion, for clinical applications.

Another means by which the elastin may be rendered suitable for injection is by digestion in pepsin or some other protease with elastase activity. Digestion of purified elastin with pepsin at room temperature or at 37° C. for between 1-5 hours generates elastin fragments of molecular weight greater than 100,000. Elastin fragments are then purified from residual pepsin utilizing size-exclusion dialysis membranes, and then concentrated to a final concentration of approximately 10 mg/mL or greater in a physiologically acceptable carrier such as 0.9% saline. Suspended elastin fragments are then combined with precipitated collagen or collagen-containing solution to produce a final product with a concentration of collagen 20 mg/mL, and a concentration of elastin 10 mg/mL, in saline with 0.3% lidocaine. The collagen-elastin composite is then dispensed into sterile syringes and packaged in sterile fashion, for clinical applications.

We claim:

1. An injectable composition comprising isolated human elastin and a pharmaceutically acceptable carrier in solution, wherein said human elastin is isolated from human vascular tissue, which has not been frozen, by decellularizing the vascular tissue, exposing said decellularized tissue to a strong base and subsequently exposing the tissue to a primary alcohol and, wherein the human elastin is substantially insoluble in water with a molecular weight greater than 100 kDa.

2. The composition of claim 1, wherein the isolated human elastin is cross-linked.

3. The composition of claim 1, wherein the composition comprises about 2 to about 60 mg/ml of isolated human elastin.

4. The composition of claim 1, wherein the composition comprises about 3 to 30 mg/ml of isolated human elastin.

5. The composition of claim 1, wherein the composition further comprises isolated human glycosaminoglycans.

6. The composition of claim 1, wherein the composition further comprises adipose tissue.

7. The composition of claim 1 wherein the composition further comprises dermal fibroblasts.

8. The composition of claim 1, wherein the composition further comprises one or more active agents selected from the group consisting of one or more anti-inflammatory agents, tissue formation agents, adipose tissue formation agents, anesthetics, antioxidants, heparin, epidermal growth factor, transforming growth factor, transforming growth factor-β, platelet-derived growth factor, fibroblast growth factor, connective tissue activating peptides, β-thromboglobulin, insulin-like growth factors, tumor necrosis factors, interleukins, colony stimulating factors, erythropoietin, nerve growth factors, interferons or combinations thereof.

9. A dermal or subdermal filler comprising the composition of claim 1.

10. The composition of claim 1, wherein said elastin does not induce calcification in vivo in a human.

11. A kit for augmentation of a soft tissue comprising the composition of claim 1, a syringe, a sterile wrapper surrounding said syringe and providing a sterile environment for said syringe.

12. The kit of claim 11 comprising agents selected from the group consisting of heparin, epidermal growth factor, transforming growth factor-alpha, transforming growth factor-beta, platelet-derived growth factor, fibroblast growth factor, connective tissue activating peptides, β-thromboglobulin, insulin-like growth factors, tumor necrosis factors, interleukins, colony stimulating factors, erythropoietin, nerve growth factors, interferons, osteogenic factors and bone morphogenic proteins.

13. The composition of claim 1, wherein said strong base is NaOH.

14. The composition of claim 1, wherein said primary alcohol is ethanol.

15. The composition of claim 1, wherein said human vascular tissue is human aorta.

16. The composition of claim 1, further comprising isolated human collagen in a mixture with said isolated human elastin and said pharmaceutically acceptable carrier in solution.

17. The composition of claim 16, wherein the isolated human collagen is isolated from micro-bead culture.

18. The composition of claim 16, wherein the isolated human collagen has a molecular weight of about 100 to about 500 kDa.

19. The composition of claim 16, wherein the composition comprises about 10-100 mg/ml of isolated human collagen.

20. The composition of claim 16, wherein the composition comprises about 30 mg/ml of isolated human collagen.

* * * * *